(12) United States Patent
Mortensen

(10) Patent No.: US 11,420,868 B2
(45) Date of Patent: Aug. 23, 2022

(54) METHOD FOR THE PREPARATION OF SYNTHESIS GAS

(71) Applicant: Haldor Topsøe A/S, Kgs. Lyngby (DK)

(72) Inventor: Peter Mølgaard Mortensen, Roskilde (DK)

(73) Assignee: Topsoe A/S, Kgs. Lyngby (DK)

( * ) Notice: Subject to any disclaimer, the term of this patent is extended or adjusted under 35 U.S.C. 154(b) by 0 days.

(21) Appl. No.: 17/281,518

(22) PCT Filed: Oct. 8, 2019

(86) PCT No.: PCT/EP2019/077154
§ 371 (c)(1),
(2) Date: Mar. 30, 2021

(87) PCT Pub. No.: WO2020/078764
PCT Pub. Date: Apr. 23, 2020

(65) Prior Publication Data
US 2022/0041440 A1    Feb. 10, 2022

(30) Foreign Application Priority Data
Oct. 15, 2018   (DK) .......................... PA 2018 00726

(51) Int. Cl.
| | |
|---|---|
| *C01B 3/36* | (2006.01) |
| *C25B 15/08* | (2006.01) |
| *C25B 1/23* | (2021.01) |
| *B01J 19/24* | (2006.01) |
| *C07C 29/151* | (2006.01) |
| *C25B 1/02* | (2006.01) |

(52) U.S. Cl.
CPC ............. *C01B 3/36* (2013.01); *B01J 19/2415* (2013.01); *C07C 29/1518* (2013.01); *C25B 1/02* (2013.01); *C25B 1/23* (2021.01); *C25B 15/081* (2021.01); *C25B 15/083* (2021.01); *C01B 2203/0216* (2013.01); *C01B 2203/061* (2013.01); *C01B 2203/062* (2013.01); *C01B 2203/0844* (2013.01)

(58) Field of Classification Search
CPC ............. C01B 3/36; C01B 2203/0216; C01B 2203/061; C01B 2203/062; C01B 2203/0844; C01B 2203/0244; C01B 2203/141; C25B 1/02; C25B 1/23; C25B 15/081; C25B 15/083; C25B 1/00; Y02P 20/133
See application file for complete search history.

(56) References Cited

U.S. PATENT DOCUMENTS

| | | | |
|---|---|---|---|
| 2003/0065042 | A1 | 4/2003 | Shaw |
| 2013/0345324 | A1 | 12/2013 | Knudsen et al. |
| 2013/0345325 | A1 | 12/2013 | Lecomte et al. |
| 2015/0329979 | A1 | 11/2015 | Reytier et al. |

FOREIGN PATENT DOCUMENTS

| | | |
|---|---|---|
| DE | 42 35 125 A1 | 4/1994 |
| EP | 2 166 064 A1 | 3/2010 |
| EP | 2 676 924 A1 | 12/2013 |
| WO | WO 2012/084135 A1 | 6/2012 |
| WO | WO 2017/144403 A1 | 8/2017 |

*Primary Examiner* — Jafar F Parsa
(74) *Attorney, Agent, or Firm* — Blank Rome LLP

(57) ABSTRACT

Method for the preparation of synthesis gas combining electrolysis of carbon dioxide, autothermal reforming and 5 optionally tubular steam reforming of a hydrocarbon feed stock.

14 Claims, No Drawings

METHOD FOR THE PREPARATION OF SYNTHESIS GAS

The present application is directed to the preparation of synthesis gas. More particular, the invention combines electrolysis of carbon dioxide and autothermal reforming and optionally additionally tubular steam reforming and/or heat exchange reforming of a hydrocarbon feed stock in the preparation of a hydrogen and carbon oxides containing synthesis gas rich in carbon monoxide.

Production of synthesis gas e.g. for the methanol synthesis with natural gas feed is typically carried out by steam reforming.

The principal reaction of steam reforming is (given for methane):

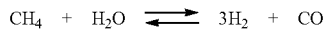

$$CH_4 + H_2O \rightleftharpoons 3H_2 + CO$$

Similar reactions occur for other hydrocarbons. Steam reforming is normally accompanied by the water gas shift reaction:

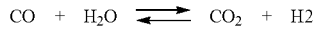

$$CO + H_2O \rightleftharpoons CO_2 + H_2$$

Steam reforming can e.g. be performed by a combination of a tubular reformer (also called steam methane reformer, SMR) and autothermal reforming (ATR), also known as primary and secondary reforming or 2-step reforming. Alternatively, stand-alone SMR or stand-alone ATR can be used to prepare the synthesis gas. Alternatively, heat exchange reforming (HTER) can be used in combination with either ATR or SMR, where the hot synthesis gas from one of these reformers is used as heating gas to facilitate the reforming reaction in the HTER.

Regardless of whether stand-alone SMR, 2-step reforming, or stand-alone ATR is used, the product gas will comprise hydrogen, carbon monoxide, and carbon dioxide as well as other components normally including hydrocarbons and steam.

Methanol synthesis gas has preferably a composition corresponding to a so-called module (M=$(H_2-CO_2)/(CO+CO_2)$) of 1.90-2.20 or more preferably slightly above 2 (eg. 2.00-2.10).

Steam reforming in an SMR typically results in a higher module i.e. excess of hydrogen, while 2-step reforming can provide the desired module. In 2-step reforming, the exit temperature of the steam reformer is typically adjusted such that the desired module is obtained at the outlet of the ATR.

In 2-step reforming, the steam methane reformer (SMR) must be large and a significant amount of heat is required to drive the endothermic steam reforming reaction. Hence, it is desirable if the size and duty of the steam reformer can be reduced. Furthermore, the ATR in the 2-step reforming concept requires oxygen. Today this is typically produced in a cryogenic air separation unit (ASU). The size and cost of this ASU is large. If the oxygen could be produced by other means, this would be desirable.

The present invention is a process where a $CO_2$ electrolysis unit is used in parallel to an ATR to provide a stream of CO which is used to adjust the composition of the syngas from the ATR, while the byproduct of oxygen from the $CO_2$ electrolysis unit can be used as co-feed to the ATR, which use oxygen as feed already. When a part of the carbon monoxide necessary in the synthesis gas is produced by $CO_2$ electrolysis, the size of the ATR can be decreased while the amount of oxygen to be supplied to the ATR from e.g. an ASU is less than without the CO2 electrolysis.

Thus, this invention provides a method for the preparation of synthesis gas comprising the steps of
a) providing a hydrocarbon feed stock;
(b) preparing a separate carbon monoxide containing stream and a separate oxygen containing stream by electrolysis of carbon dioxide;
(c) optionally tubular steam reforming at least a part of the hydrocarbon feed stock from step (a) to a tubular steam reformed gas upstream step (d);
(d) autothermal reforming in an autothermal reformer the hydrocarbon feed stock or the tubular steam reformed gas with at least a part of the oxygen containing stream obtained by the electrolysis of carbon dioxide in step (b) to an autothermal reformed gas stream comprising hydrogen, carbon monoxide and carbon dioxide;
(e) introducing at least part of the separate oxygen containing stream from step (b) into the autothermal reformer (f) introducing at least part of the separate carbon monoxide containing stream from step (b) into the reformed gas stream from step (d) or step (e); and
(g) withdrawing the synthesis gas.

Preferably, the synthesis gas withdrawn in step (g) has a H2/CO ratio of less than 2. Thereby addition of CO2 into the autothermal reformer can be avoided, which reduces the size of the autothermal reformer and the consumption of the hydrocarbon feedstock and oxygen.

In further an embodiment, the method according to the invention comprises the further step of heat exchange reforming at least a part of the hydrocarbon feed stock from step (a) to a heat exchange reformed gas using at least part of the autothermal reformed gas stream from step (d) in combination with the heat exchange reformed gas as heating source for the heat exchange reformer to provide a reformed gas.

The oxygen containing stream from step (b) may in some instances contain $CO_2$, $H_2O$, or $N_2$, depending on the specific configuration of the $CO_2$ electrolysis unit. Similarly, the carbon monoxide containing stream from step (b) may contain $CO_2$.

In some applications, the oxygen prepared by electrolysis of $CO_2$ introduced into the autothermal reformer in step (d) can additionally be supplemented by oxygen prepared by air separation in an (ASU).

Thus in an embodiment of the invention, the method according to the invention comprises the further step of separating air into a separate stream containing oxygen and into a separate stream containing nitrogen and introducing at least a part of the separate stream containing oxygen into the autothermal reformer in step (d).

A suitable hydrocarbon feed stock comprises natural gas, methane, LNG, naphtha or mixtures thereof either as such or pre-reformed and/or steam reformed and/or desulfurized.

The hydrocarbon feed stocks may further comprise hydrogen and/or steam as well as other components.

Like the electrolysis of $CO_2$, the air separation can preferably be at least powered by renewable energy. In all the above embodiments, a part of the hydrocarbon feed stock from step (a) can bypass the optional tubular steam reforming in step (c) if employed and introduced to the autothermal reformer in step (d)

The amount of hydrogen added to the reformed gas downstream step (d) can be tailored such that when the hydrogen is mixed with the process gas generated by the reforming step(s), the desired value of M of between 1.90 and 2.20 or preferably between 2 and 2.1 is achieved.

The module can additionally be adjusted to the desired value by introducing substantially pure carbon dioxide upstream step (c), and/or upstream of step (d) and/or downstream step (d).

In one embodiment, the electrolysis is operated such that total amount of the separate carbon monoxide containing stream from step (b) is added to the autothermal reformed gas stream downstream step (d) to provide a module of $H_2$ to CO (H2/CO) in the synthesis gas withdrawn from step (f) of between 1.9 and 2.2, preferably of 2.0.

In this embodiment, some or preferably all the oxygen from the electrolysis unit is added to the autothermal reformer in step (d). Additional oxygen from an air separation unit can be added to the autothermal reformer in this embodiment.

The electrolysis can be performed by various means known in the art such as by solid oxide based electrolysis.

If the power for the electrolysis is produced (at least in part) by sustainable sources, the $CO_2$-emissions is per unit of product produced by the method reduced.

The method according to the invention is preferably employed for the production of methanol by conversion of the synthesis gas withdrawn in step (g).

However, the method can also be employed for producing synthesis gas for other applications where it is desirable to increase the hydrogen concentration in the feed gas and where part of the oxygen and hydrogen needed for synthesis gas production is favorably produced by electrolysis.

Thus, in an embodiment of the invention the synthesis gas withdrawn in step (f) is in a further step converted to a Fischer-Tropsch product.

EXAMPLE

The Table below shows an example of the process production of a synthesis gas of $H_2/CO=1.0$. A first ATR produces a first synthesis gas. In parallel, the $CO_2$ electrolysis produces a second synthesis gas stream of primarily $CO_2$ mixed with CO. When combining the second synthesis gas stream with the first synthesis gas stream, the final synthesis gas is obtained with a lower $H_2/CO$ ratio than the first.

|  | ATR | CO2 electrolysis | Combined synthesis gas product |
| --- | --- | --- | --- |
| Inlet T [° C.] | 625 | 850 |  |
| Outlet T [° C.] | 1050 | 850 |  |
| Inlet P [barg] | 34.5 | 5 |  |
| Outlet P [barg] | 33.5 | 5 |  |
| Inlet: |  |  |  |
| $N_2$ [Nm³/h] | 0 | 0 |  |
| $CO_2$ [Nm³/h] | 682 | 1000 |  |
| $CH_4$ [Nm³/h] | 916 | 0 |  |
| $H_2$ [Nm³/h] | 0 | 0 |  |
| CO [Nm³/h] | 0 | 0 |  |
| $H_2O$ [Nm³/h] | 550 | 0 |  |
| Oxygen feed: |  |  |  |
| $O_2$ T [° C.]: | 240 |  |  |
| $O_2$ [Nm³/h] | 571* |  |  |
| $N_2$ [Nm³/h] | 10 |  |  |
| $H_2O$ [Nm³/h] | 5 |  |  |
| Outlet: |  |  |  |
| $N_2$ [Nm³/h] | 10 | 0 | 10 |
| $CO_2$ [Nm³/h] | 453 | 800 | 1253 |
| $CH_4$ [Nm³/h] | 9 | 0 | 9 |
| $H_2$ [Nm³/h] | 1349 | 0 | 1349 |
| CO [Nm³/h] | 1135 | 200 | 1335 |
| $H_2O$ [Nm³/h] | 1018 | 0 | 1018 |
| $O_2$ [Nm³/h] | 0 | 100** | 0 |
| Total outlet [Nm³/h] | 3974 | 1100 | 4974 |

*100 Nm³/h supplied from CO2 electrolysis.
**Separate outlet.

COMPARISON EXAMPLE

For comparison, the example below shows a single ATR for production of the same amount of synthesis gas (H2+CO) also at a H2/CO ratio of 1.0. Comparing the two tables, it can be seen that the combination of ATR and CO2 electrolysis gives a smaller ATR (exemplified by the lower total flow out of the ATR), but consequently also uses less oxygen and additionally supplies ca. 18% of the oxygen directly from the $CO_2$ electrolysis unit. The required oxygen supply is consequently significantly decreased.

|  | Stand-alone ATR |
| --- | --- |
| Inlet T [° C.] | 625 |
| Outlet T [° C.] | 1050 |
| Inlet P [barg] | 34.5 |
| Outlet P [barg] | 33.5 |
| Inlet: |  |
| $N_2$ [Nm³/h] | 0 |
| $CO_2$ [Nm³/h] | 1000 |
| $CH_4$ [Nm³/h] | 1000 |
| $H_2$ [Nm³/h] | 0 |
| CO [Nm³/h] | 0 |
| $H_2O$ [Nm³/h] | 600 |
| Oxygen feed: |  |
| $O_2$ T [° C.]: | 240 |
| $O_2$ [Nm³/h] | 645 |
| $N_2$ [Nm³/h] | 13 |
| $H_2O$ [Nm³/h] | 6 |
| Outlet: |  |
| $N_2$ [Nm³/h] | 13 |
| $CO_2$ [Nm³/h] | 655 |
| $CH_4$ [Nm³/h] | 7 |
| $H_2$ [Nm³/h] | 1346 |
| CO [Nm³/h] | 1338 |
| $H_2O$ [Nm³/h] | 1247 |
| Total outlet [Nm³/h] | 4606 |

The invention claimed is:

1. A method for the preparation of synthesis gas comprising the steps of
    (a) providing a hydrocarbon feed stock;
    (b) preparing a separate carbon monoxide containing stream and a separate oxygen containing stream by electrolysis of carbon dioxide;
    (c) optionally tubular steam reforming at least a part of the hydrocarbon feed stock from step (a) to a tubular steam reformed gas upstream step (c);
    (d) autothermal reforming in an autothermal reformer the hydrocarbon feed stock or the optionally tubular steam reformed gas with at least a part of the oxygen containing stream obtained by the electrolysis of carbon dioxide in step (b) to an autothermal reformed gas stream comprising hydrogen, carbon monoxide and carbon dioxide;

(e) introducing at least part of the separate oxygen containing stream from step (b) into the autothermal reformer (f) introducing at least part of the separate carbon monoxide containing stream from step (b) into the autothermal reformed gas stream from step (d); and (g) withdrawing the synthesis gas.

2. The method of claim 1, wherein the H2/CO ratio is less than 2.

3. The method of claim 1, comprising the further step of heat exchange reforming at least a part of the hydrocarbon feed stock from step (a) to a heat exchange reformed gas using at least part of the autothermal reformed gas stream from step (d) in combination with the heat exchange reformed gas as heating source for the heat exchange reformer to provide a reformed gas.

4. The method of claim 1, comprising the further step of separating air into a separate stream containing oxygen and into a separate stream containing nitrogen and introducing at least a part of the separate stream containing oxygen into the autothermal reformer in step (d).

5. The method of claim 1, wherein a part of the hydrocarbon feed stock from step (a) is bypassed the optional tubular steam reforming in step (c) and introduced to the autothermal reformer in step (d).

6. The method of claim 1, wherein the hydrocarbon feed stock comprises natural gas, methane, LNG, naphtha or mixtures thereof either as such or pre-reformed and/or steam reformed and/or desulfurized.

7. The method of claim 1, wherein the electrolysis of carbon dioxide in step (b) is powered at least in part by renewable energy.

8. The method of claim 1, wherein the separating of air is powered at least in part by renewable energy.

9. The method of claim 1, comprising the further step of introducing substantially pure carbon dioxide upstream step (c), and/or upstream of step (d), and/or downstream step (d).

10. The method of claim 1, wherein the electrolysis is operated such that all of the separate carbon monoxide containing stream from step (b) is added to the autothermal reformed gas stream downstream step (d) to provide a module $M=(H_2-CO_2)/(CO+CO_2)$ in the synthesis gas withdrawn from step (f) of between 1.9 and 2.2.

11. The method of claim 1, wherein the module $M=(H_2-CO_2)/(CO+CO_2)$ in the synthesis gas withdrawn in step (f) is in the range from 2 to 2.1.

12. The method of claim 1, wherein the synthesis gas withdrawn in step (g) is in a further step converted to a methanol product.

13. The method of claim 1, wherein the electrolysis is operated such that all of the separate carbon monoxide containing stream from step (b) is added to the autothermal reformed gas stream downstream step (d) to provide a module H2 to CO (H2/CO) in the synthesis gas withdrawn from step (g) of between 1.9 and 2.2.

14. The method of claim 1, wherein the synthesis gas withdrawn in step (g) is in a further step converted to a Fischer-Tropsch product.

* * * * *